United States Patent
Snoonian et al.

(10) Patent No.: US 7,115,746 B2
(45) Date of Patent: Oct. 3, 2006

(54) PROCESSES FOR THE FACILE SYNTHESIS OF DIARYL AMINES AND ANALOGUES THEREOF

(75) Inventors: John R. Snoonian, Ayer, MA (US); Patricia Ann Oliver-Shaffer, Acton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 10/775,687

(22) Filed: Feb. 10, 2004

(65) Prior Publication Data

US 2004/0230058 A1 Nov. 18, 2004

Related U.S. Application Data

(60) Provisional application No. 60/474,272, filed on May 28, 2003, provisional application No. 60/446,641, filed on Feb. 10, 2003.

(51) Int. Cl.
*C07D 213/02* (2006.01)

(52) U.S. Cl. .................. 546/312; 546/304; 546/310

(58) Field of Classification Search ................ 546/310, 546/312, 304
See application file for complete search history.

(56) References Cited

FOREIGN PATENT DOCUMENTS

WO   WO 02/14281 A1   2/2002

OTHER PUBLICATIONS

Cao et al, Bioorganic & Medicinal Chemistry Letters, vol. 11, pp. 3169-3173, 2001.*
Cao, Jianjing et al., "[3-*cis*-3,5-dimethyl-(1-piperazinyl)alkyl]-bis-(4'-fluorophenyl)amine analogues as novel probes for the dopamine transporter," Bioorg. & Med. Chem. Lett. 11:3169-73 (2001).
Sucholeiki, Irving et al., "New polyoxyalkyleneamine-grafted paramagnetic supports for solid-phase synthesis and bioapplications," Tetrahedron Lett. 42: 3279-82 (2001).
Beilstein Database Accession No. Beilstein Reaction ID 4342815.
Seto, Christopher T. et al., "Molecular self-assembly through hydrogen bonding: Aggregation of five molecules to form a discrete supramolecular structure," J. Am. Chem. Soc. 113: 1321-29 (1993).
Rewcastle, Gordon W. et al., "Potential antitumor agents. 52. Carbamate analogues of amsacrine with in vivo activity against multidrug-resistant P388 leukemia," J. Med. Chem. 30:1576-81 (1987).

* cited by examiner

*Primary Examiner*—Zinna N. Davis
(74) *Attorney, Agent, or Firm*—Karen E. Brown; Vertex Pharmaceuticals Incorporated

(57) ABSTRACT

The present invention relates to processes for the facile synthesis of diaryl amines and analogues thereof. The processes of the present invention produce diaryl amines in high yield and purity. The present invention also relates to intermediates useful in the process of the present invention.

59 Claims, No Drawings

PROCESSES FOR THE FACILE SYNTHESIS OF DIARYL AMINES AND ANALOGUES THEREOF

CROSS-REFERENCE TO RELATED APPLICATIONS

The present application claims the benefit of U.S. provisional application Ser. No. 60/446,641, filed Feb. 10, 2003, and U.S. provisional application Ser. No. 60/474,272, filed May 28, 2003, the entire contents whereof is incorporated herein by reference.

TECHNICAL FIELD OF THE INVENTION

The present invention relates to processes for the facile synthesis of diaryl amines and analogues thereof. The processes of the present invention produce diaryl amines in high yield and purity. The present invention also relates to intermediates useful in the process of the present invention. The present invention also relates to a diaryl amines produced by the processes of the present invention.

BACKGROUND OF THE INVENTION

Protein kinases are involved in various cellular responses to extracellular signals. Recently, a family of mitogen-activated protein kinases (MAPK) has been discovered. Members of this family are Ser/Thr kinases that activate their substrates by phosphorylation [B. Stein et al., Ann. Rep. Med. Chem., 31, pp. 289–98 (1996)]. MAPKs are themselves activated by a variety of signals including growth factors, cytokines, UV radiation, and stress-inducing agents.

One particularly interesting MAPK is p38. p38, also known as cytokine suppressive anti-inflammatory drug binding protein (CSBP) and RK, was isolated from murine pre-B cells that were transfected with the lipopolysaccharide (LPS) receptor, CD14, and induced with LPS. p38 has since been isolated and sequenced, as has the cDNA encoding it in humans and mice. Activation of p38 has been observed in cells stimulated by stress, such as treatment of lipopolysaccharides (LPS), UV, anisomycin, or osmotic shock, and by cytokines, such as IL-1 and TNF.

Inhibition of p38 kinase leads to a blockade on the production of both IL-1 and TNF. IL-1 and TNF stimulate the production of other proinflammatory cytokines such as IL-6 and IL-8 and have been implicated in acute and chronic inflammatory diseases and in post-menopausal osteoporosis [R. B. Kimble et al., Endocrinol., 136, pp. 3054–61 (1995)].

Based upon this finding, it is believed that p38, along with other MAPKs, have a role in mediating cellular response to inflammatory stimuli, such as leukocyte accumulation, macrophage/monocyte activation, tissue resorption, fever, acute phase responses and neutrophilia. In addition, MAPKs, such as p38, have been implicated in cancer, thrombin-induced platelet aggregation, immunodeficiency disorders, autoimmune disease, cell death, allergies, osteoporosis and neurodegenerative diseases. Inhibitors of p38 have also been implicated in the area of pain management through inhibition of prostaglandin endoperoxide synthase-2 induction. Other disease associated with IL-1, IL-6, IL-8 or TNF overproduction are set forth in WO 96/21654.

Many molecules possessing medicinally important properties against various targets, including MAPKs, comprise diaryl amines. One example of this is a class of molecules identified as potent p38 MAP kinase inhibitors (see, e.g., WO 99/58502 and WO 00/17175). However, although they are effective as drugs, there are few ways to make aryl amine-containing molecules without a significant amount of by-product. Palladium-catalyzed couplings of an aryl amine and aryl halide have been the traditional strategy to produce a molecule comprising a diaryl amine. However, problems with over-addition of the aryl halide partner to the amine have traditionally resulted in low yields and purities when a primary aryl amine is employed. For this reason, primary amines are not commonly employed substrates for this transformation, which has limited the scope of the palladium-catalyzed coupling reaction.

Accordingly, the need exists for a process for the facile synthesis of diaryl amines and analogues thereof that avoids the problem of over-arylation, to obtain diaryl amines in high yield and purity. There also exists a need for intermediates produced by such a process.

SUMMARY OF THE INVENTION

According to one embodiment, the present invention provides processes for the facile synthesis of diaryl amines that avoid the problem of over-arylation, are amenable to large scale preparation, and provide high yields. The present invention also avoids the use of harmful reagents such as tin compounds. Specifically, the present invention provides a process wherein a primary aryl amine is rendered temporarily "secondary" by adding a suitable protecting group to the nitrogen. Once formed, this protected aniline derivative undergoes an alkali metal salt-promoted or transition metal-catalyzed cross coupling with an aryl leaving group to produce an intermediate, which, upon deprotection, produces the diaryl amine substrate. The product may be produced with few by-products and in high yield.

The invention provides processes for producing a compound of the formula (I):

or a salt thereof, wherein:

Ar$_1$ and Ar$_2$ are as defined below.

The processes of this invention comprise the step of coupling a compound of formula (II) with an amine of formula (III) to obtain a diaryl amine of formula (I), in the presence of an alkali metal salt or transition metal catalyst:

wherein:

Ar$_1$, Ar$_2$, X, and Y are as defined below.

The processes of this invention have the advantages of allowing preparation of a compound of formula (I) from a primary aryl amine derivative without the problem of over-arylation. The processes of this invention have the further advantage of allowing preparation of a compound of formula (I) in high yield and purity, in addition to facile reaction conditions that are readily scaled up for large scale preparation.

DETAILED DESCRIPTION OF THE INVENTION

The present invention overcomes the difficulties and shortcomings of the prior art and provides processes for producing a compound of the formula (I):

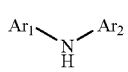
(I)

or a salt thereof, wherein:

$Ar_1$ and $Ar_2$ are independently Q;

wherein each Q is an aryl or heteroaryl ring system optionally fused to a saturated or unsaturated 5–8 membered ring having 0–4 heteroatoms;

wherein Q is optionally substituted at one or more ring atoms with one or more substituents independently selected from halo; $C_1$–$C_6$ aliphatic optionally substituted with $N(R')_2$, $OR'$, $CO_2R'$, $C(O)N(R')_2$, $OC(O)N(R')_2$, $NR'CO_2R'$, $NR'C(O)R'$, $SO_2N(R')_2$, $N=CH-N(R')_2$, or $OPO_3H_2$; $C_1$–$C_6$ alkoxy optionally substituted with $N(R')_2$, $OR'$, $CO_2R'$, $C(O)N(R')_2$, $OC(O)N(R')_2$, $SO_2N(R')_2$, $NR'CO_2R'$, $NR'C(O)R'$, $N=CH-N(R')_2$, or $OPO_3H_2$; $Ar_3$; $CF_3$; $OCF_3$; $OR'$; $SR'$; $SO_2N(R')_2$; $OSO_2R'$; $SCF_3$; $NO_2$; $CN$; $N(R')_2$; $CO_2R'$; $CO_2N(R')_2$; $C(O)N(R')_2$; $NR'C(O)R'$; $NR'CO_2R'$; $NR'C(O)C(O)R'$; $NR'SO_2R'$; $OC(O)R'$; $NR'C(O)R^2$; $NR'CO_2R^2$; $NR'C(O)C(O)R^2$; $NR'C(O)N(R')_2$; $OC(O)N(R')_2$; $NR'SO_2R^2$; $NR'R^2$; $N(R^2)_2$; $OC(O)R^2$; $OPO_3H_2$; and $N=CH-N(R')_2$;

R' is selected from hydrogen; $C_1$–$C_6$ aliphatic; or a 5–6 membered carbocyclic or heterocyclic ring system optionally substituted with 1 to 3 substituents independently selected from halo, $C_1$–$C_6$ alkoxy, cyano, nitro, amino, hydroxy, and $C_1$–$C_6$ aliphatic;

$R^2$ is a $C_1$–$C_6$ aliphatic optionally substituted with $N(R')_2$, $OR'$, $CO_2R'$, $C(O)N(R')_2$ or $SO_2N(R')_2$; or a carbocyclic or heterocyclic ring system optionally substituted with $N(R')_2$, $OR'$, $CO_2R'$, $C(O)N(R')_2$ or $SO_2N(R')_2$;

wherein $Ar_3$ is an aryl or heteroaryl ring system optionally fused to a saturated or unsaturated 5–8 membered ring having 0–4 heteroatoms;

wherein $Ar_3$ is optionally substituted at one or more ring atoms with one or more substituents independently selected from halo; $C_1$–$C_6$ aliphatic optionally substituted with $N(R')_2$, $OR'$, $CO_2R'$, $C(O)N(R')_2$, $OC(O)N(R')_2$, $NR'CO_2R'$, $NR'C(O)R'$, $SO_2N(R')_2$, $N=CH-N(R')_2$, or $OPO_3H_2$; $C_1$–$C_6$ alkoxy optionally substituted with $N(R')_2$, $OR'$, $CO_2R'$, $C(O)N(R')_2$, $OC(O)N(R')_2$, $SO_2N(R')_2$, $NR'CO_2R'$, $NR'C(O)R'$, $N=CH-N(R')_2$, or $OPO_3H_2$; $CF_3$; $OCF_3$; $OR'$; $SR'$; $SO_2N(R')_2$; $OSO_2R'$; $SCF_3$; $NO_2$; $CN$; $N(R')_2$; $CO_2R'$; $C_2N(R')_2$; $C(O)N(R')_2$; $NR'C(O)R'$; $NR'CO_2R'$; $NR'C(O)C(O)R'$; $NR'SO_2R'$; $OC(O)R'$; $NR'C(O)R^2$; $NR'CO_2R^2$; $NR'C(O)C(O)R^2$; $NR'C(O)N(R')_2$; $OC(O)N(R')_2$; $NR'SO_2R^2$; $NR'R^2$; $N(R^2)_2$; $OC(O)R^2$; $OPO_3H_2$; and $N=CH-N(R')_2$.

In a preferred embodiment, $Ar_1$ and $Ar_2$ are independently selected from optionally substituted phenyl, naphthyl, benzimidazolyl, benzothienyl, benzofuranyl, indolyl, quinolinyl, benzothiazolyl, benzooxazolyl, benzimidazolyl, isoquinolinyl, isoindolyl, acridinyl, benzoisoxazolyl, pyridyl, pyrimidyl, pyridazinyl, tetrazolyl, furanyl, imidizaolyl, isoxazolyl, oxadiazolyl, oxazolyl, pyrrolyl, thiazolyl, triazolyl, and thienyl. In a more preferred embodiment, $Ar_1$ and $Ar_2$ are independently selected from optionally substituted phenyl and pyridyl. In an even more preferred embodiment, $Ar_1$ is optionally substituted pyridyl and $Ar_2$ is optionally substituted phenyl.

The processes of this invention comprise the step of coupling a compound of formula (II) with an amine of formula (III) to obtain a diaryl amine of formula (I), in the presence of an alkali metal salt or transition metal catalyst:

$Ar_1-X$      (II)

$Ar_2-NH-Y$      (III)

wherein:

X is a leaving group; and

Y is $-C(O)-O-Z$; and

Z is selected from $C_1$–$C_6$ aliphatic, benzyl, Fmoc, $-SO_2R'$ and Q, provided that Q is not substituted with X or alkyne; wherein $Ar_1$, $Ar_2$, Q and R' are as defined above.

Scheme 1 below depicts a preferred process of the present invention:

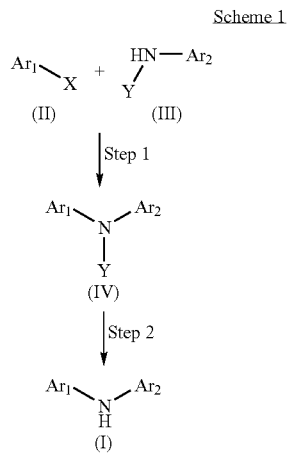

wherein $Ar_1$, $Ar_2$, X, and Y are as defined above. The steps illustrated above may be described as follows:

Step 1:

A compound of formula (II), bearing a suitable leaving group X, is reacted with a compound of formula (III), which bears the Y—NH-moiety. The reaction is conducted in the presence of an alkali metal salt, such as cesium carbonate; or alternatively a transition metal catalyst, and optionally a base and optionally one or more ligands.

In one embodiment, a transition metal catalyst is used. An exemplary transition metal catalyst that can be used comprises a transition metal ion or atom and one or more suitable ligands. Preferably, the transition metal catalyst comprises a Group 8 metal. More preferably, the transition metal catalyst comprises palladium. According to a preferred embodiment, two different ligands are simultaneously used in step 1.

According to a preferred embodiment, a base is used in step 1 in conjunction with the transition metal catalyst. Suitable bases include KOtBu, NaOtBu, $K_3PO_4$, $Na_2CO_3$, and $Cs_2CO_3$. More preferably, the base is $K_3PO_4$.

Preferred solvents for step 1 when using a transition metal catalyst include toluene and non-polar aprotic solvents such as MTBE, DME, and hexane.

In another embodiment, an alkali metal salt is used in step 1. Preferably, the alkali metal salt is a cesium salt.

Preferred solvents for step 1 when using an alkali metal salt include polar aprotic solvents such as NMP.

Step 2:

In step 2, radical Y of (IV) is removed to produce the diaryl amine of formula (I).

According to a preferred embodiment, an acid, such as TFA, HCl, HBr, or HI is used in step 2. More preferably, the acid is TFA.

Preferred solvents for step 2 include chlorinated solvents such as $CH_2Cl_2$, 1,2-dichloroethane, and chlorobenzene.

The processes of this invention have the advantages of allowing preparation of a compound of formula (I) from a primary aryl amine derivative without the problem of over-arylation. The processes of this invention have the further advantage of allowing preparation of a compound of formula (I) in high yield and purity, and on a large scale.

Step 1 Reagents:

Transition metal catalysts suitable for the present invention comprise a transition metal atom or ion and one or more ligands. The transition metal may exist in any suitable oxidation state ranging from zero valence to any higher valence available to the transition metal. According to a preferred embodiment, the transition metal catalyst comprises a Group 8 metal. More preferably, the transition metal catalyst comprises palladium. Catalyst complexes may include chelating ligands, including, without limitation, alkyl and aryl derivatives of phosphines and biphosphines, imines, arsines, and hybrids thereof.

More preferably, the transition metal catalyst is a palladium catalyst of the formula $PdL_n$, wherein each L is independently selected from Cl, —OAc, —O-tolyl, halogen, $PPh_3$, dppe, dppf, and BINAP; and n is an integer from 1–4. The aforementioned transition metal catalysts may be prepared using methods known in the art.

A variety of ligand transformations may occur throughout the process of the present invention. The ligand may be bound to the transition metal throughout the process of the present invention, or the ligand may be in a labile configuration in relation to the transition metal during all or part of the process. Accordingly, the term "transition metal catalyst" as used herein includes any transition metal catalyst and/or catalyst precursor as it is introduced into the reaction vessel and which is, if necessary, converted in situ into the active form of catalyst that participates in the reaction.

The quantity of the transition metal catalyst to be used in the present process is any quantity that promotes the formation of the diaryl amine product. According to a preferred embodiment, the quantity is a catalytic amount, wherein the catalyst is used in an amount that is less than stoichiometric relative to the aryl components. In another preferred embodiment, the catalyst is present in the range of about 0.01 to about 20 mole percent relative to the non-amine aryl component, more preferably about 1 to about 10 mole percent, and even more preferably about 1 to about 5 mole percent.

One of skill in the art may readily select an appropriate solvent to use in the process of the present invention. A solvent may be present in any quantity need to facilitate the desired process, and does not necessarily have to be a quantity to dissolve the substrates and/or reagents of the desired process. A solvent according to the present invention will not interfere with the formation of the diaryl amine product. Examples of suitable solvents include, without limitation, halogenated solvents, hydrocarbon solvents, ether solvents, protic solvents, and aprotic solvents. Mixtures of solvents are also included within the scope of this invention. Preferred solvents useful for Step 1 of the process of the present invention using a transition metal catalyst include toluene, benzene, or a non-polar aprotic solvent such as MTBE, DME, or hexane.

According to one embodiment, the coupling step using a transition metal catalyst (Step 1) occurs in the presence of a base. Examples of suitable bases include, without limitation, alkali metal hydroxides, alkali metal alkoxides, metal carbonates, phosphates, alkali metal aryl oxides, alkali metal amides, tertiary amines, (hydrocarbyl)ammonium hydroxides, and diaza organic bases. The quantity of base used may be any quantity which allows for the formation of the diaryl amine product. Preferred bases of the present invention include KOtBu, NaOtBu, $K_3PO_4$, $Na_2CO_3$, and $Cs_2CO_3$.

Alkali metal salts suitable for the present invention comprise salts of sodium, potassium, rubidium or cesium ions. Preferably, alkali metal salts suitable for the present invention comprise salts of potassium or cesium ions. Preferred alkali metal salts comprise carbonate, phosphate, and alkoxide salts. More preferred alkali metal salts suitable include potassium carbonate and cesium carbonate. Most preferably, the alkali metal salt is cesium carbonate.

The quantity of the transition metal catalyst to be used in the present process is any quantity that promotes the formation of the diaryl amine product.

Preferred solvents useful for Step 1 of the process of the present invention using an alkali metal salt include polar aprotic solvents such as NMP.

Step 2 Reagents:

According to a preferred embodiment, the protecting group removal step (Step 2) occurs in the presence of an acid. Examples of suitable acids include, without limitation, HCl, HBr, HI, and organic acids including formic acid, acetic acid, propionic acid, butanoic acid, methanesulfonic acid, p-toluene sulfonic acid, benzenesulfonic acid, and trifluoroacetic acid. Preferred acids of the present invention include HCl, HBr, HI, and TFA.

Preferred solvents for Step 2 of the process of the present invention include chlorinated solvents such as $CH_2Cl_2$, 1,2-dichloroethane, and chlorobenzene.

In one embodiment of the present invention, X is a leaving group. According to a preferred embodiment, X is selected from the group consisting of Cl, Br, I, F, OTf, OTs, iodonium, and diazo.

In one embodiment of the present invention, Y is a carbamate amine protecting group. According to a preferred embodiment, Y is Boc.

As used herein, the following definitions shall apply unless otherwise indicated. Also, combinations of substituents are permissible only if such combinations result in stable compounds.

Some of the abbreviations used throughout the specification (including the chemical formulae) are:

Boc=t-butoxycarbonyl
Fmoc=fluorenylmethoxycarbonyl
Tf=trifluoromethanesulfonate
Ts=p-toluenesulfonyl
Ms=methanesulfonyl
TFA=trifluoroacetic acid
Ac=acetyl
dba=trans,trans-dibenzylideneacetone
dppe=1,2-bis-(diphenylphosphino)ethane
dppf=1,1'-bis-(diphenylphosphanyl)ferrocene
dppp=propane-1,3-diylbis(diphenylphosphane)

BINAP=2,2'-bis(diphenylphosphanyl)-1,1'-binaphthyl
MTBE=methyl t-butyl ether
DME=dimethoxyethane
CDI=1,1'-carbonyl-diimidazole
DCC=N,N'-dicyclohexylcarbodiimide
EDC=1-ethyl-3-(3-dimethylaminopropyl)carbodiimide hydrochloride
HOBt=N-hydroxybenzotriazole
NMP=N-methylpyrrolidinone
DMF=dimethylformamide
MCPBA=m-chloroperbenzoic acid
MMPP=magnesium monoperoxyphthalate hexahydrate
DIBAL-H=diisobutyl aluminum hydride
LAH=lithium aluminum hydride
super hydride=lithium triethylborohydride
L-selectride=lithium tri-sec-butylborohydride
Red-Al=sodium bis(methoxyethoxy)aluminum hydride
IPA=isopropanol
glyme=dimethoxy ethane
diglyme=bis(2-methoxy ethyl)ether As used herein, the following definitions shall apply unless otherwise indicated. The phrase "optionally substituted" is used interchangeably with the phrase "substituted or unsubstituted." Also, combinations of substituents are permissible only if such combinations result in chemically stable compounds. In addition, unless otherwise indicated, functional group radicals are independently selected.

The term "leaving group", as used herein, has the definition known to those of ordinary skill in the art (see, March, Advanced Organic Chemistry, 4$^{th}$ Edition, John Wiley & Sons, pp. 352–357, 1992, herein incorporated by reference). Examples of leaving groups include, without limitation, halogens such as F, Cl, Br, and I, diazo, aryl- and alkyl-sulfonyloxy groups, and trifluoromethanesulfonyloxy.

The term "aliphatic" as used herein means straight-chain or branched $C_1$–$C_{12}$ hydrocarbon chain that is completely saturated or that contains one or more units of unsaturation. The term "aliphatic" also includes a monocyclic $C_3$–$C_8$ hydrocarbon or bicyclic $C_8$–$C_{12}$ hydrocarbon that is completely saturated or that contains one or more units of unsaturation, but which is not aromatic (said cyclic hydrocarbon chains are also referred to herein as "carbocycle" or "cycloalkyl"), that has a single point of attachment to the rest of the molecule wherein any individual ring in said bicyclic ring system has 3–7 members. For example, suitable aliphatic groups include, but are not limited to, linear or branched alkyl, alkenyl, alkynyl groups and hybrids thereof such as (cycloalkyl)alkyl, (cycloalkenyl)alkyl) or (cycloalkyl)alkenyl.

The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms, wherein an alkenyl comprises at least one double bond and an alkynyl comprises at least one triple bond.

The term "chemically stable" or "chemically feasible and stable", as used herein, refers to a compound structure that renders the compound sufficiently stable to allow manufacture and administration to a mammal by methods known in the art. Typically, such compounds are stable at temperature of 40° C. or less, in the absence of moisture or other chemically reactive conditions, for at least a week.

The term "haloalkyl", "haloalkenyl", and "haloalkoxy", means alkyl, alkenyl, or alkoxy, as the case may be, substituted with one or more halogen atoms. The term "halogen" means F, Cl, Br, or I.

The term "heteroatom" means N, O, or S and shall include any oxidized form of nitrogen and sulfur, and the quaternized form of any basic nitrogen.

The term "amine" or "amino" used alone or as part of a larger moiety, refers to a trivalent nitrogen, which may be primary or which may be substituted with 1–2 aliphatic groups.

The term "aryl" used alone or as part of a larger moiety as in "aralkyl", "aralkoxy", or "aryloxyalkyl", refers to monocyclic, bicyclic, and tricyclic carbocyclic ring systems having a total of five to fourteen members, where at least one ring in the system is aromatic and wherein each ring in the system contains 3 to 8 ring members. The term "aryl" may be used interchangeably with the term "aryl ring".

The term "heterocycle", "heterocyclyl", or "heterocyclic" as used herein means non-aromatic, monocyclic, bicyclic, or tricyclic ring systems having five to fourteen ring members in which one or more of the ring members is a heteroatom, wherein each ring in the system contains 3 to 7 ring members.

One having ordinary skill in the art will recognize that the maximum number of heteroatoms in a stable, chemically feasible heterocyclic or heteroaromatic ring is determined by the size of the ring, degree of unsaturation, and valence of the heteroatoms. In general, a heterocyclic or heteroaromatic ring may have one to four heteroatoms so long as the heterocyclic or heteroaromatic ring is chemically feasible and stable.

The term "heteroaryl", used alone or as part of a larger moiety as in "heteroaralkyl" or "heteroarylalkoxy", refers to monocyclic, bicyclic and tricyclic ring systems having a total of five to fourteen ring members, and wherein at least one ring in the system is aromatic, at least one ring in the system contains one or more heteroatoms, and each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroarylalkyl and heteroarylalkoxy and the like) group may contain one or more substituents. Suitable substituents on the unsaturated carbon atom of an aryl, heteroaryl, aralkyl, or heteroaralkyl group are selected from halogen; haloalky; —$CF_3$; —$R^4$; —$OR^4$; —$SR^4$; 1,2-methylenedioxy; 1,2-ethylenedioxy; protected OH (such as acyloxy); phenyl (Ph); Ph substituted with $R^4$; —OPh; —OPh substituted with $R^4$; —$CH_2$Ph; —$CH_2$Ph substituted with $R^4$; —$CH_2CH_2$(Ph); —$CH_2CH_2$(Ph) substituted with $R^4$; —$NO_2$; CN; N(R')$_2$; —$NR^4C(O)R^4$; —$NR^4C(O)N(R^4)_2$; —$NR^4CO_2R^4$; —$NR^4NRC(O)R^4$; —$NR^4C(O)N(R^4)_2$; —$NR^4NR^4C(O)R^4$; —$NR^4NR^4C(O)N(R^4)_2$; —$NR^4NR^4CO_2R^4$; —C(O)C(O)$R^4$—C(O)$CH_2$C(O)R'; —$CO_2R'$; —C(O)R'; —C(O)N(R')$_2$; —OC(O)N($R^4$)$_2$; —$SO_2R'$; —$SO_2N(R')_2$; —S(O)$R^4$; —$NR^4SO_2N(R')_2$; —$NR^4SO_2R^4$; —C(=S)N(R')$_2$; —C(=NH)—N(R')$_2$; —$(CH_2)_y$NHC(O)$R^4$; —$(CH_2)_yR^4$; —$(CH_2)_y$NHC(O)NHR$^4$; —$(CH_2)_y$NHC(O)OR$^4$; —$(CH_2)_y$NHS(O)$R^4$; —$(CH_2)_y$NHSO$_2R^4$; or —$(CH_2)_y$NHC(O)CH(V—$R^4$)$R^4$;

wherein each R⁴ is independently selected from hydrogen, optionally substituted $C_{1-6}$ aliphatic, an unsubstituted 5–6 membered heteroaryl or heterocyclic ring, phenyl (Ph), —O—Ph, —$CH_2$ (Ph); wherein y is 0–6; and V is a linker group. When R⁴ is $C_{1-6}$ aliphatic, it may be substituted with one or more substituents selected from —$NH_2$, —NH($C_{1-4}$ aliphatic), —N($C_{1-4}$ aliphatic)$_2$, —S(O) ($C_{1-4}$ aliphatic), —$SO_2$($C_{1-4}$ aliphatic), halogen, —($C_{1-4}$ aliphatic), —OH, —O—($C_{1-4}$ aliphatic), —$NO_2$, —CN, —$CO_2$H, —$CO_2$($C_{1-4}$ aliphatic), —O-(halo $C_{1-4}$ aliphatic), or -halo($C_{1-4}$ aliphatic); wherein each $C_{1-4}$ aliphatic is unsubstituted.

The term "linker group" or "linker" means an organic moiety that connects two parts of a compound. Linkers are comprised of —O—, —S—, —NR*—, —C(R*)$_2$—, —C(O), or an alkylidene chain. The alkylidene chain is a saturated or unsaturated, straight or branched, $C_{1-6}$ carbon chain which is optionally substituted, and wherein up to two non-adjacent saturated carbons of the chain are optionally replaced by —C(O)—, —C(O)C(O)—, —C(O)NR*—, —C(O)NR*NR*—, NR*NR*—, —NR*C(O)—, —S—, —SO—, —$SO_2$—, —NR*—, —$SO_2$NR*—, or —NR*$SO_2$—; wherein R* is selected from hydogen or aliphatic. Optional substituents on the alkylidene chain are as described below for an aliphatic group.

An aliphatic group or a non-aromatic heterocyclic ring may contain one or more substituents. Suitable substituents on the saturated carbon of an aliphatic group or of a non-aromatic heterocyclic ring are selected from those listed above for the unsaturated carbon of an aryl or heteroaryl group and the following: =O, =S, =NNHR⁵, =NN(R⁵)$_2$, =NR⁵, —OR⁵, =NNHC(O)R⁵, =NNHCO$_2$R⁵, =NNHSO$_2$R⁵, or =NR⁵, where each R⁵ is independently selected from hydrogen or a optionally substituted $C_{1-6}$ aliphatic. When R⁵ is $C_{1-6}$ aliphatic, it may be substituted with one or more substituents selected from —$NH_2$, —NH ($C_{1-4}$ aliphatic), —N($C_{1-4}$ aliphatic)$_2$, halogen, —OH, —O—($C_{1-4}$ aliphatic), —$NO_2$, —CN, —$CO_2$H, —$CO_2$($C_{1-4}$ aliphatic), —O-(halo $C_{1-4}$ aliphatic), or (halo $C_{1-4}$ aliphatic); wherein each $C_{1-4}$ aliphatic is unsubstituted.

Substituents on the nitrogen of a non-aromatic heterocyclic ring are selected from —R⁶, —N(R⁶)$_2$, —C(O)R⁶, —CO$_2$R⁶, —C(O)C(O)R⁶, —C(O)CH$_2$C(O)R⁶, —SO$_2$R⁶, —SO$_2$N(R⁶)$_2$, —C(=S)N(R')$_2$, —C(=NH)—N(R')$_2$, or —NRSO$_2$R; wherein each R⁶ is independently selected from hydrogen, an optionally substituted $C_{1-6}$ aliphatic, optionally substituted phenyl (Ph), optionally substituted —O—Ph, optionally substituted —$CH_2$ (Ph), or an unsubstituted 5–6 membered heteroaryl or heterocyclic ring. When R⁶ is a $C_{1-6}$ aliphatic group or a phenyl ring, it may be substituted with one or more substituents selected from —$NH_2$, —NH($C_{1-4}$ aliphatic), —N($C_{1-4}$ aliphatic)$_2$, halogen, —($C_{1-4}$ aliphatic), —OH, —O—($C_{1-4}$ aliphatic), —$NO_2$, —CN, —$CO_2$H, —$CO_2$($C_{1-4}$ aliphatic), —O-halo($C_{1-4}$ aliphatic), or (halo $C_{1-4}$ aliphatic); wherein each $C_{1-4}$ aliphatic is unsubstituted.

Schemes 2–8 illustrate the application of the process of Scheme 1 to the synthesis of pyridinyl aryl amine derivatives. These pyridinyl diaryl amines synthesized according to the present invention may be further functionalized according to methods known to those of skill in the art in order to produce compounds that are potent inhibitors of p38 kinase.

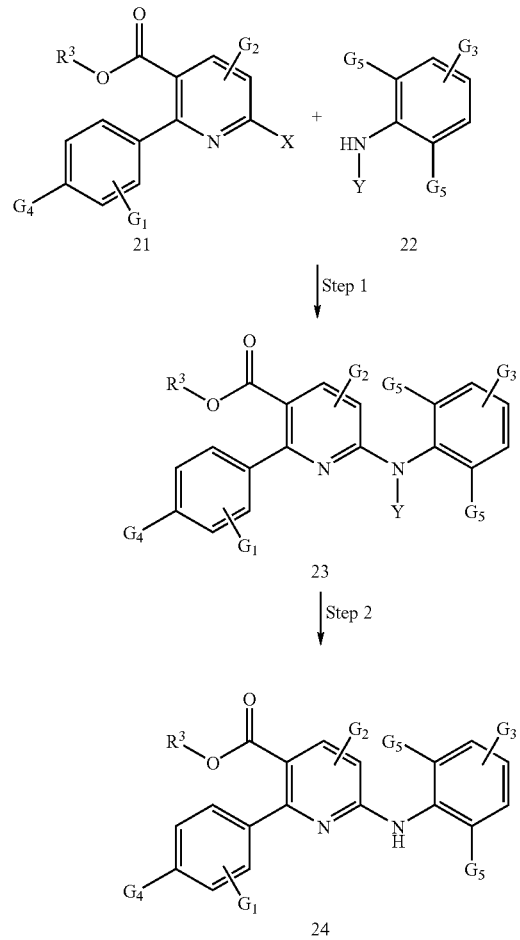

Scheme 2 wherein:
R³ is selected from $C_1$–$C_6$ aliphatic; aryl; and aryl substituted with $C_1$–$C_6$ aliphatic, aryl, nitro, CN, CO$_2$R', CO$_2$N(R')$_2$, OR', NCO$_2$R', NR'C(O)N(R')$_2$, or OC(O)N(R')$_2$;

provided that R³ is not t-butyl;

G$_1$, G$_2$, G$_3$, G$_4$, and G$_5$ are independently selected from hydrogen, aliphatic, aryl, substituted aryl, nitro, CN, OR', CO$_2$R', CO$_2$N(R')$_2$, NR'CO$_2$R', NR'C(O)N(R')$_2$, OC(O)N(R')$_2$, F, Cl, Br, I, O-Ts, O-Ms, OSO$_2$R', and OC(O)R';

X is a leaving group;

Y is —C(O)—O-Z;

Z is selected from $C_1$–$C_6$ aliphatic, benzyl, Fmoc, —SO$_2$R' or Q, provided that Q is not substituted with X or alkyne;

wherein Q and R' are as defined above.

The various steps illustrated in Scheme 2 may be described as follows:

Step 1: The starting material 21 is available by synthesis from 2-chloronicotinic acid according to procedures known in the art (see, e.g., Scheme 3). The starting material 21 is coupled with a protected aryl amine 22 (see, e.g., Scheme 3) in the presence of an alkali metal salt such as cesium carbonate in a solvent such as NMP; or alternatively in the presence of a catalyst such as palladium acetate, optionally a ligand such as BINAP or dppe, and optionally a base such as potassium phosphate in a compatible solvent such as toluene, MTBE, DME, or hexane, to give the protected coupling product of formula 23.

Step 2: The protected coupling product 23 is reacted with an acid such as TFA in a suitable solvent such as methylene chloride, 1,2-dichloroethane, or chlorobenzene, to give the compound of formula 24.

Scheme 3a illustrates the synthesis of starting material 21 and Scheme 3b exemplifies the further derivatization of deprotected coupling product 24 of Scheme 2.

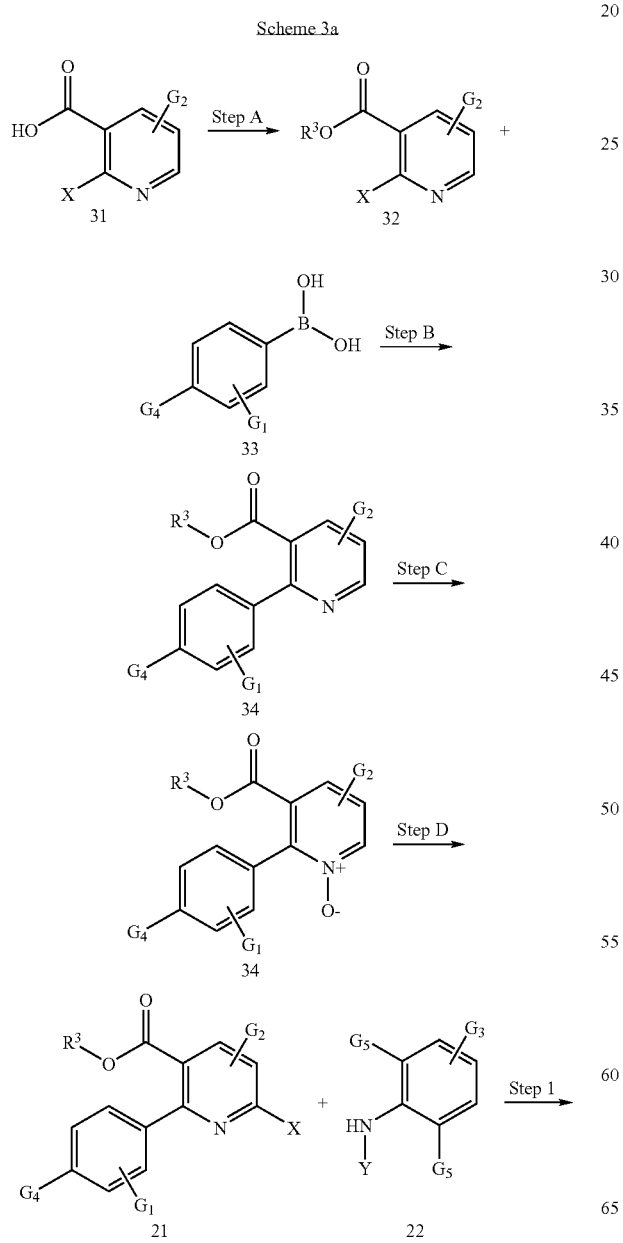

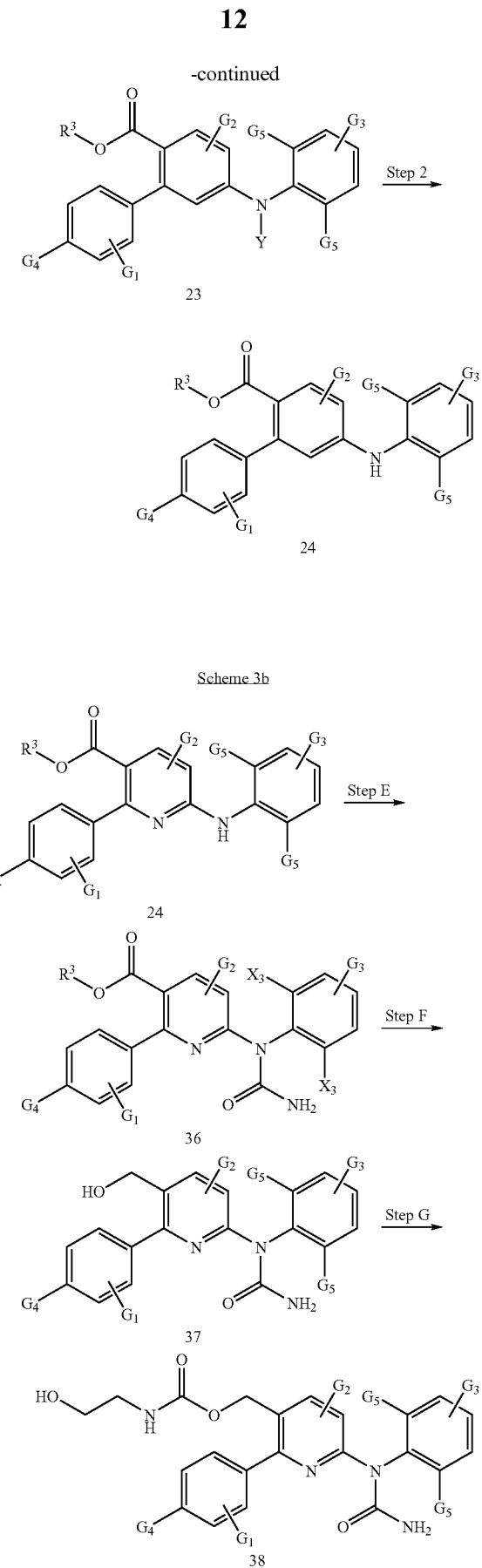

wherein $R^3$, $G_1$, $G_2$, $G_3$, $G_4$, and $G_5$ are as set forth in Scheme 2 above.

The various steps illustrated in Schemes 3a and 3b may be described as follows:

Step A: Nicotinic acid derivative 31 may be activated by reacting it with a chloroformate activating agent such as $SOCl_2$, phenylchloroformate, or p-nitrophenyl chloroformate, or a carbodiimide activating agent such as CDI, DCC, or EDC in the presence of HOBt and N-hydroxysuccinimide in a polar aprotic solvent such as $CH_2Cl_2$, 1,2-dichloroethane, DMF, or NMP, and heating. An alcohol of the formula $R^3OH$ is then added to form compound 32.

Step B: Compound 32 is coupled with a boronic acid such as 33 in the presence of a catalyst such as palladium acetate, a base such as sodium carbonate, potassium carbonate, lithium carbonate, cesium carbonate, potassium t-butoxide, sodium t-butoxide, or lithium t-butoxide in a solvent such as toluene, MTBE, DME, or hexane to give 34.

Step C: Coupled product 34 is then N-oxidized in the presence of a reagent such as MCPBA, peracetic acid, or MMPP in a chlorinated solvent such as $CH_2Cl_2$ or 1,2-dichloroethane to give 35.

Step D: N-oxide 35 is activated in the presence of a reagent such as $POCl_3$, $POBr_3$, $SOCl_2$, $SO_2Cl_2$, or $SOBr_2$ to give 21.

Steps 1 and 2 are as set forth in Scheme 2 above.

Step E: The free amine of 24 is derivatized to form the corresponding urea by reaction with an activated carbonyl such as $X_4C(O)X_5$, wherein $X_4$ and $X_5$ are each independently selected from Cl, Br, I, imidazole, O-Ph, p-nitrophenyloxy, substituted O-aryl, or a leaving group, and then reacting the carbonyl with ammonium hydroxide in a solvent such as toluene, DME, or MTBE to form 36.

Step F: The ester functionality of 36 is reduced to the corresponding alcohol in the presence of a reducing agent such as DIBAL, LAH, super hydride, L-Selectide, $LiBH_4$, $NaBH_3$(anilide), Red-Al, or $NaBH_4$ in a solvent such as THF, DME, MTBE, MeOH, EtOH, IPA, t-BuOH, glyme, or diglyme to form 37.

Step G: The alcohol of 37 may be further functionalized such as by activation with $X_4C(O)X_5$, wherein $X_4$ and $X_5$ are as described in step E above, then reacting the carbonyl with $OH(CH_2)_2NH_2$ to form 38.

Although the processes of schemes 4–7 are illustrated using specific reagents and starting materials, it will be appreciated by one of skill in the art that suitable analogous reactants and starting materials may be used to prepare analogous compounds.

Scheme 4 provides an example using the method of the instant invention to produce a diaryl amine.

Scheme 4

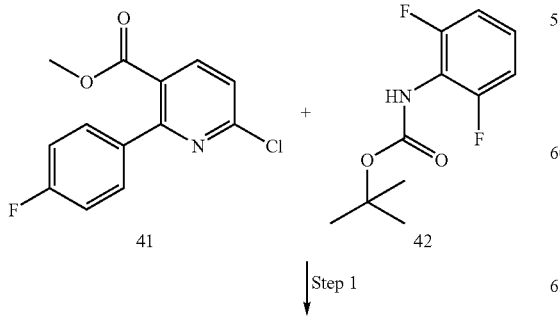

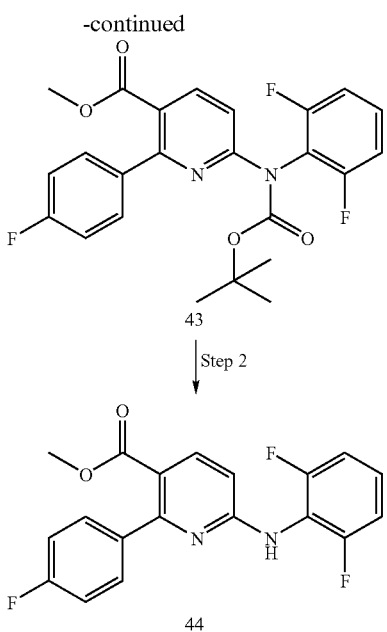

The various steps illustrated in Scheme 4 may be briefly described as follows:

Step 1: 6-chloro-2-(4-fluorophenyl)-nicotinic acid methyl ester 41 is available by synthesis from 2-chloronicotinic acid (see, e.g., Scheme 5). 41 is coupled with a protected aryl amine such as Boc-2,6-difluoroaniline 42 (see, e.g., Scheme 5) in the presence of an alkali metal salt such as cesium carbonate and a solvent such as NMP; or alternatively in the presence of a catalyst such as palladium acetate, optionally a ligand such as BINAP, and optionally a base such as potassium phosphate in a compatible solvent such as toluene to give the protected coupling product of formula 43.

Step 2: Protected coupling product 43 is reacted with an acid such as TFA in a suitable solvent such as methylene chloride to give the compound of formula 44.

More generally, one of skill in the art will recognize that the compound of formula 44 may be produced by the reaction of 41a with 42a:

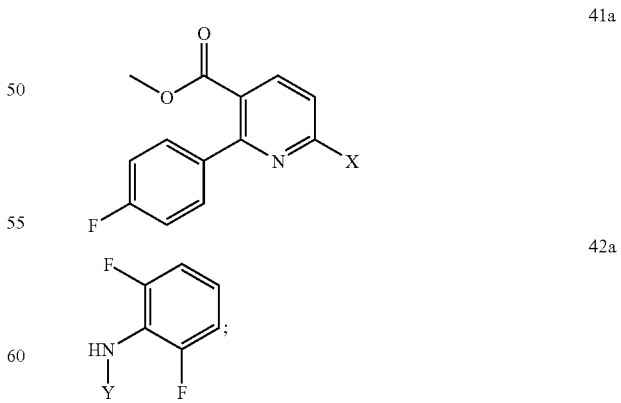

wherein X and Y are as set forth above.

Scheme 5a illustrates the synthesis of starting material 41 and Scheme 5b illustrates the further derivatization of the deprotected coupling product 44 of Scheme 4.

Scheme 5a

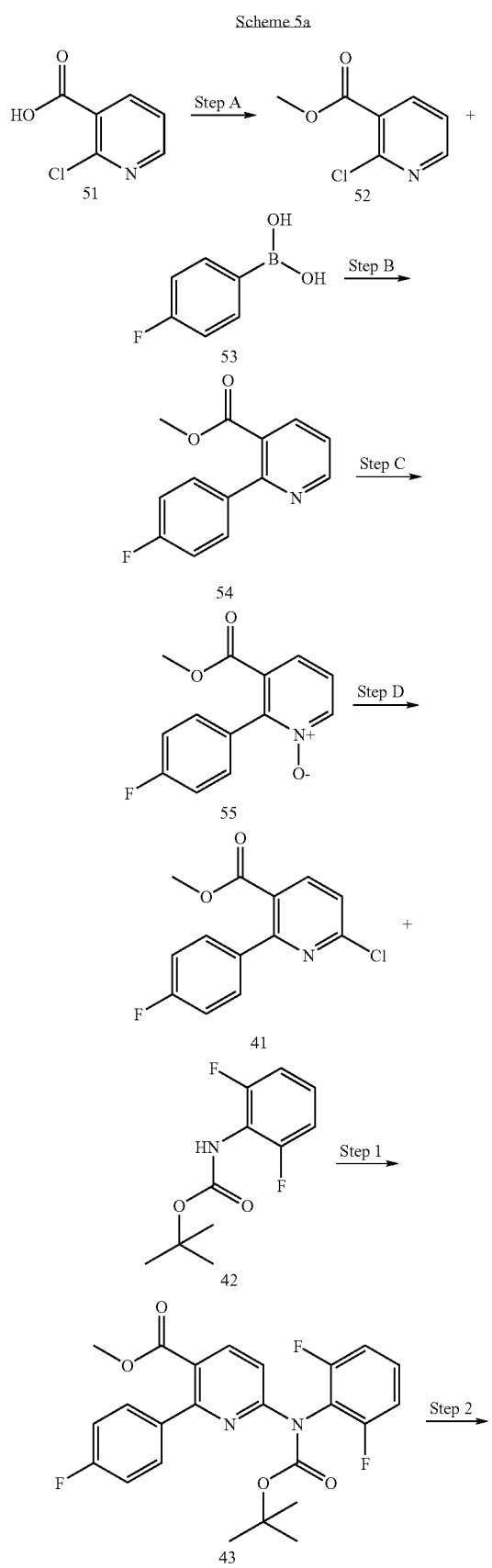

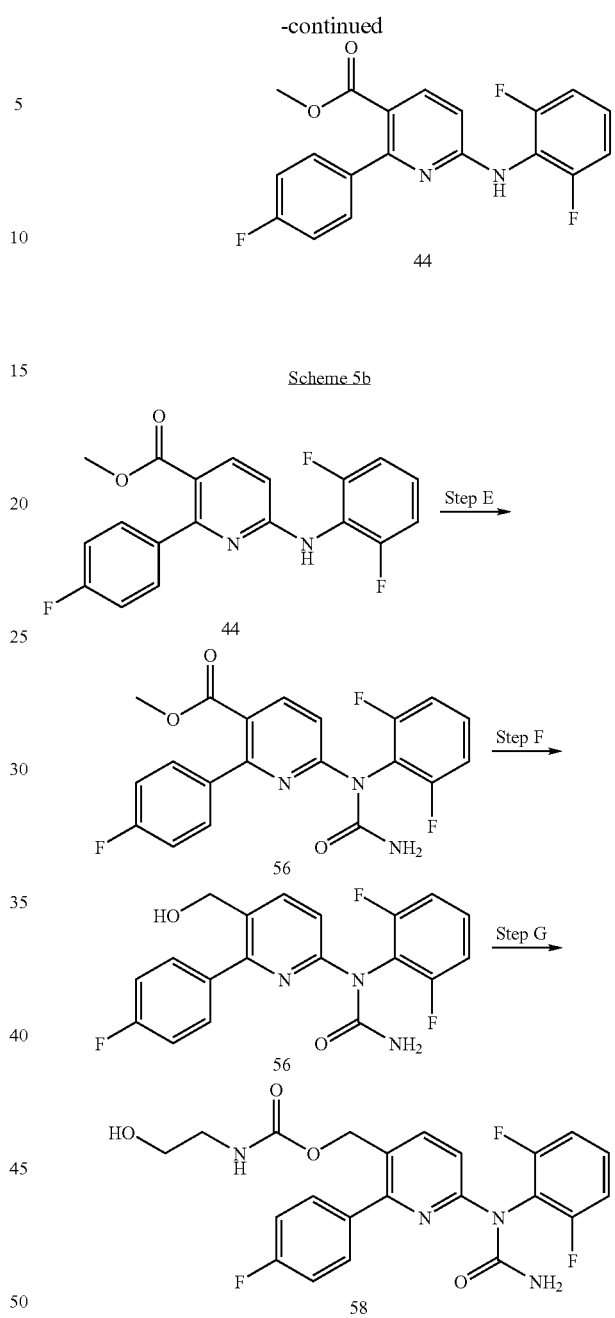

Scheme 5b

The various steps illustrated in Schemes 5a and 5b may be briefly described as follows:

Step A: 6-Chloronicotinic acid 51 is activated by reacting with a chloroformate activating agent such as $SOCl_2$, phenylchloroformate, or p-nitrophenyl chloroformate, or a carbodiimide activating agent such as CDI, DCC, or EDC in the presence of HOBt and N-hydroxysuccinimide in a polar aprotic solvent such as $CH_2Cl_2$, 1,2-dichloroethane, DMF, or NMP, and heating. An alcohol such as methanol is then added to form 6-chloronicotinic acid methyl ester 52.

Step B: Compound 52 is coupled with a boronic acid such as 53 in the presence of a catalyst such as palladium acetate, a base such as sodium carbonate, potassium carbonate, lithium carbonate, cesium carbonate, potassium t-butoxide, sodium t-butoxide, or lithium t-butoxide in a solvent such as toluene, MTBE, DME, or hexane to give 54.

Step C: The coupled product 54 is then N-oxidized in the presence of a reagent such as MCPBA, peracetic acid, or MMPP in a chlorinated solvent such as $CH_2Cl_2$ or 1,2-dichloroethane to give 55.

Step D: The activated N-oxide 55 is halogenated in the presence of a reagent such as $POCl_3$, $POBr_3$, $SOCl_2$, $SO_2Cl_2$, or $SOBr_2$ to give 41.

Steps 1 and 2 are as set forth for Scheme 4 above.

Step E: The free amine of 44 is derivatized to form the corresponding urea by reaction with an activated carbonyl such as $X_4C(O)X_5$, wherein $X_4$ and $X_5$ each are independently selected from Cl, Br, I, imidazole, O-Ph, p-nitrophenyloxy, substituted O-aryl, or a leaving group, and then reacting the carbonyl with ammonium hydroxide in a solvent such as toluene, DME, or MTBE to form 56.

Step F: The ester functionality of 56 is reduced to the corresponding alcohol in the presence of a reducing agent such as DIBAL, LAH, super hydride, L-Selectide, $LiBH_4$, $NaBH_3$(anilide), Red-Al, or $NaBH_4$ in a solvent such as THF, DME, MTBE, MeOH, EtOH, IPA, t-BuOH, glyme, or diglyme to form 57.

Step G: The alcohol of 57 may be further functionalized such as by reaction with $X_4C(O)X_5$, wherein $X_4$ and $X_5$ are as described in step E above, then reacting the carbonyl with $OH(CH_2)_2NH_2$ to form 58.

Scheme 6 provides an example using the method of the instant invention to produce a diaryl amine.

-continued

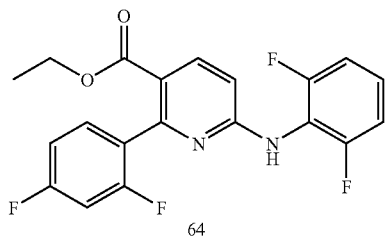

The various steps illustrated in Scheme 6 may be briefly described as follows:

Step 1: 6-chloro-2-(2,4-difluorophenyl)-nicotinic acid ethyl ester 61 is available by synthesis from 2-chloronicotinic acid (see, e.g., Scheme 7). 61 is coupled with a protected aryl amine such as Boc-2,6-difluoroaniline 42 (see, e.g., Scheme 7) in the presence of an alkali metal salt such as cesium carbonate and a solvent such as NMP; or alternatively in the presence of a catalyst such as palladium acetate, optionally a ligand such as BINAP, and optionally a base such as potassium phosphate in a compatible solvent such as toluene to give the protected coupling product of formula 62.

Step 2: The protected coupling product 62 is reacted with an acid such as TFA in a suitable solvent such as methylene chloride to give the compound of formula 63.

More generally, one of skill in the art will recognize that the compound of formula 63 may be produced by the reaction of 61a with 42a:

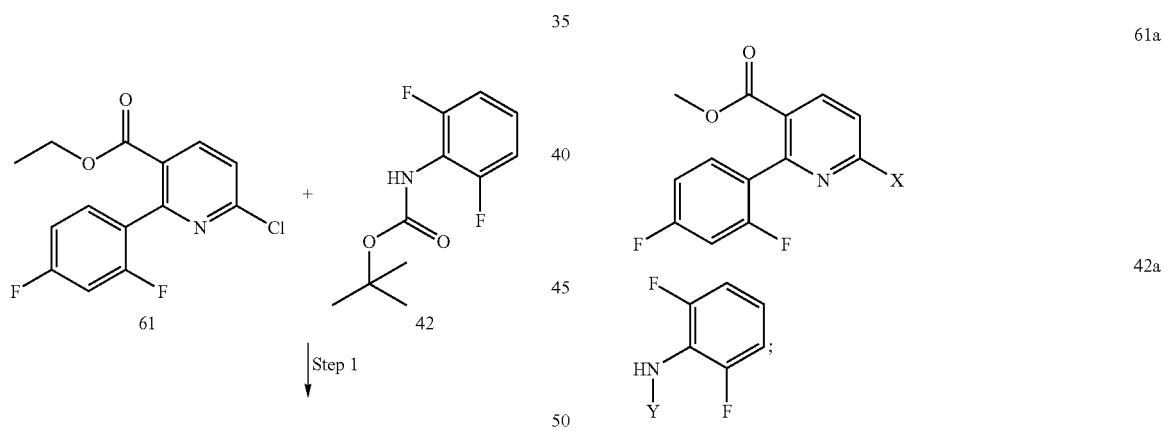

wherein X and Y are as defined above.

Scheme 7a illustrates the synthesis of starting material 61 and Scheme 7b illustrates the further derivatization of the deprotected coupling product 63 of Scheme 6.

Scheme 7a

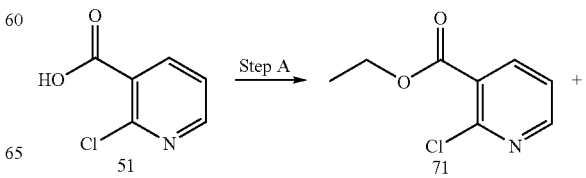

-continued

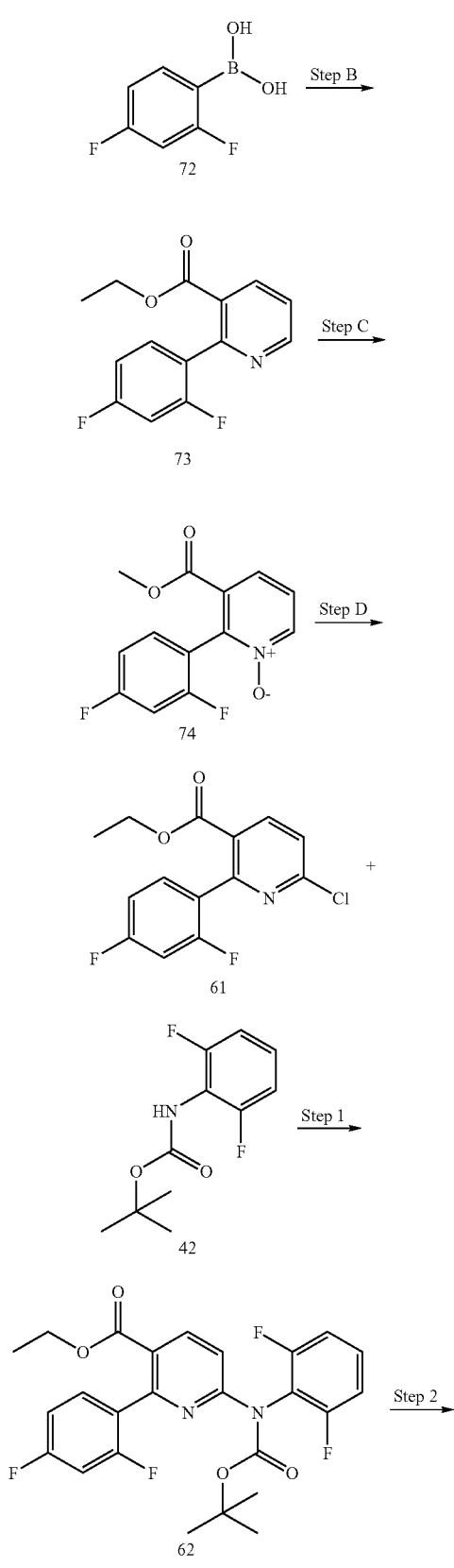

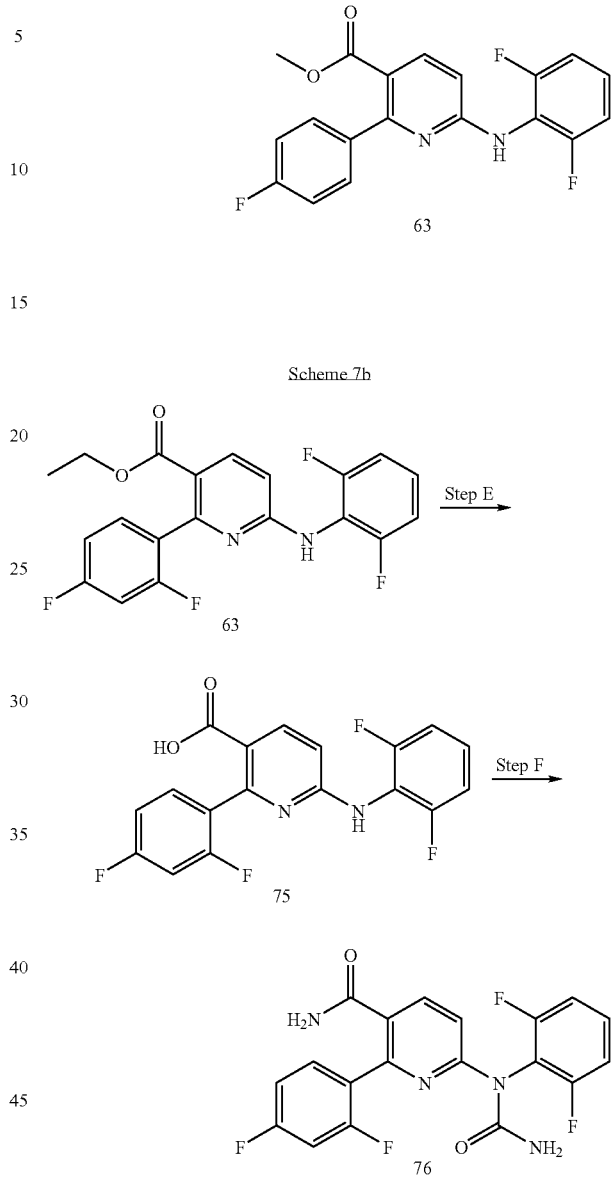

The various steps in Schemes 7a and 7b may be briefly described as follows:

Step A: 6-Chloronicotinic acid 51 is activated by reacting with a chloroformate activating agent such as $SOCl_2$, phenylchloroformate, or p-nitrophenyl chloroformate, or a carbodiimide activating agent such as CDI, DCC, or EDC in the presence of HOBt and N-hydroxysuccinimide in a polar aprotic solvent such as $CH_2Cl_2$, 1,2-dichloroethane, DMF, or NMP, and heating. An alcohol such as ethanol is then added to form 6-chloronicotinic acid ethyl ester 71.

Step B: Compound 71 is coupled with a boronic acid such as 72 in the presence of a catalyst such as palladium acetate, a base such as sodium carbonate, potassium carbonate, lithium carbonate, cesium carbonate, potassium t-butoxide, sodium t-butoxide, or lithium t-butoxide in a solvent such as toluene, MTBE, DME, or hexane to give 73.

Step C: Coupled product 73 is then N-oxidized in the presence of a reagent such as MCPBA, peracetic acid, or MMPP in a chlorinated solvent such as CH$_2$Cl$_2$ or 1,2-dichloroethane to give 74.

Step D: The activated N-oxide 74 is halogenated in the presence of a reagent such as POCl$_3$, POBr$_3$, SOCl$_2$, SO$_2$Cl$_2$, or SOBr$_2$ to give 61.

Steps 1 and 2 are as set forth for Scheme 6 above.

Step E: The ester functionality of 63 is saponified in the presence of a base such as NaOH in a solvent such as THF, and then acidified in the presence of an acid such as HCl to form 75.

Step F: 75 is then reacted with diphosgene followed by NH$_4$OH to form the amide-urea compound 76.

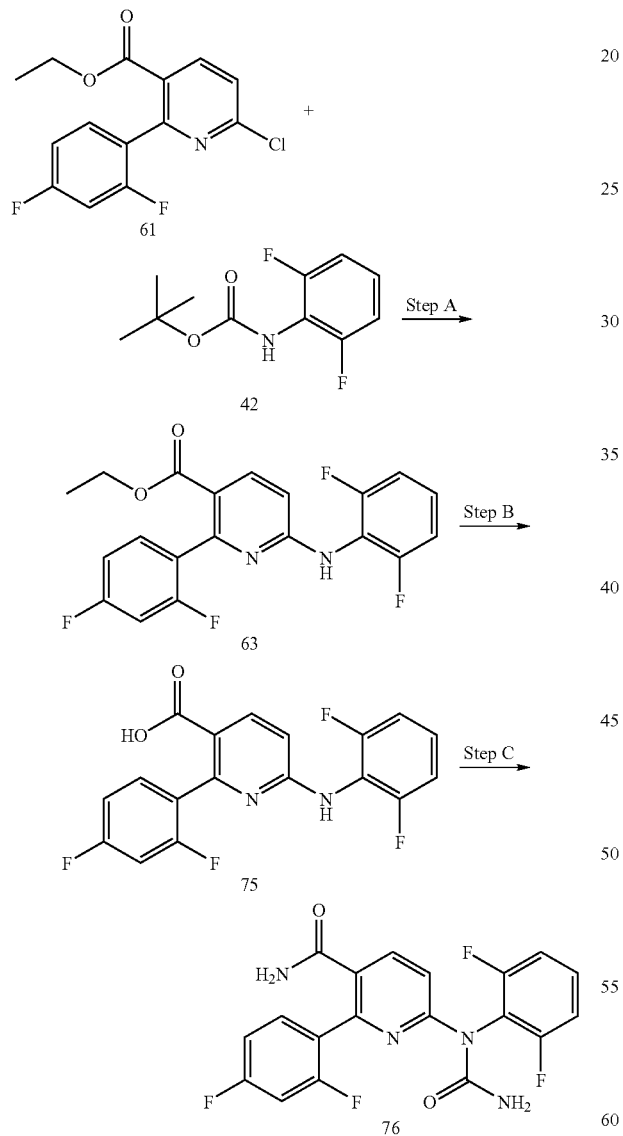

Scheme 8

The various steps in Scheme 8 may be briefly described as follows:

Step A: 6-chloro-2-(2,4-difluorophenyl)-nicotinic acid ethyl ester 61 is available by synthesis from 2-chloronicotinic acid. Starting material 61 is coupled with a protected aryl amine such as Boc-2,6-difluoroaniline 42 in the presence of an alkali metal salt such as cesium carbonate in a compatible solvent such as NMP to give the protected coupling product. The protected coupling product is then reacted with an acid such as TFA in a suitable solvent such as methylene chloride to give the compound of formula 63.

Step B: The ester functionality of 63 is saponified in the presence of a base such as NaOH in a solvent such as THF, and then acidified in the presence of an acid such as HCl to form 75.

Step C: 75 is then reacted with diphosgene followed by NH$_4$OH to form the amide-urea compound 76.

The following examples illustrate the present invention in a manner in which it may be practiced, but should not be construed as limitations upon the overall scope of the processes of the invention.

Where applicable, the following HPLC method was utilized unless otherwise indicated: a gradient of water:acetonitrile, 0.1% TFA (90:10→10:90→90:10) was run over 26 minutes at 1 mL/min and 254 nm. The method utilizes the Zorbax SB Phenyl 4.6×25 cm column, 5 μm. The term "$T_{ret}$" refers to the retention time, in minutes, associated with the compound.

According to another embodiment, the methods of of the present invention provides compounds of formula (A) or formula (B):

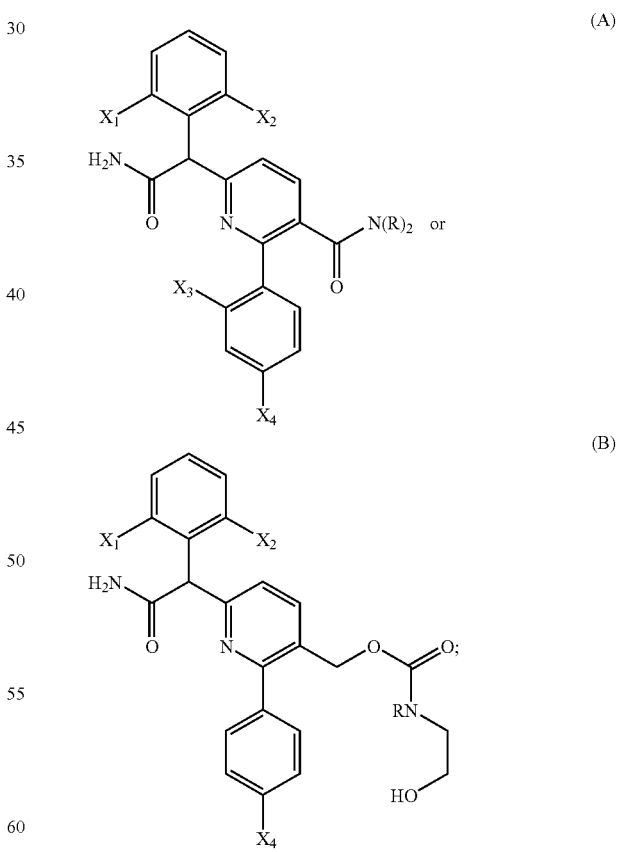

wherein:

each of $X_1$, $X_2$, $X_3$, and $X_4$ is independently selected from fluoro or chloro; and R is H or methyl.

Compounds of formula (A) and formula (B) are useful as inhibitors of p38. International PCT Publication WO 99/58502 (hereinafter "the '502 publication"), the disclosure whereof is incorporated herein by reference, discloses a genus of compounds that encompasses compounds of formula (A) and formula (B). The methods of the present invention may be readily used to produce compounds of the '502 publication.

According to a preferred embodiment of formula (A), each of $X_1$, $X_2$, $X_3$, and $X_4$ is fluoro. According to another preferred embodiment of formula (A), R is H.

According to a preferred embodiment of formula (B), each of $X_1$, $X_2$, and $X_4$ is fluoro. According to another preferred embodiment of formula (B), R is H.

According to the most preferred embodiment of formula (B), the methods of the present invention produce compound 77 below:

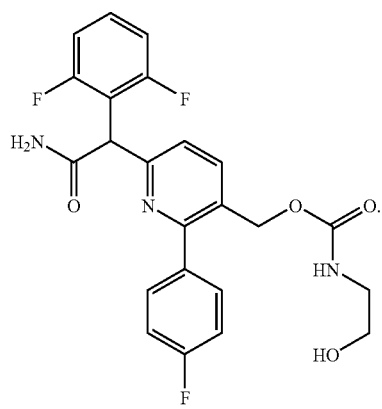

77

EXAMPLES

Example 1

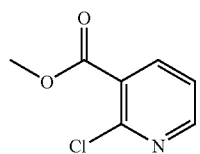

52

2-Chloro-nicotinic acid methyl ester (52): 52 was prepared according to the method of Synth. Comm. 26(12), 2257–2272 (1996). To a nitrogen purged flask was charged 2-chloro-nicotinic acid (1000.0 g, 6.0 moles, 1.0 eq) followed by 9 L methylene chloride. To this was added thionyl chloride (1.4 L, 19.7 moles, 3.2 eq.) and the reaction was heated to 40° C. with vigorous stirring under nitrogen overnight. The acid chloride solution was cooled in an ice bath and methanol (3 L, 74 moles, 12 eq.) was slowly added while keeping the temperature at 20° C. The rate limiting parameter is the vigorous evolution of copious quantities of HCl gas. After the addition, HPLC analysis [$T_{ret}$ starting material=7.5 min, $T_{ret}$ 52=11 min] showed the product had formed immediately. The volatiles were removed in vacuo and the residue extracted from 10% $Na_2CO_3$ with EtOAc. The combined organics were dried ($MgSO_4$), filtered, and concentrated to a pale yellow oil.

Example 2

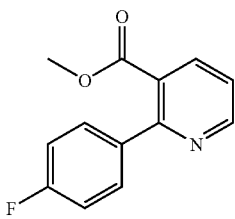

54

2-(4-Fluoro-phenyl)-nicotinic acid methyl ester (54): To a nitrogen purged flask was charged $Pd(Ph_3)_4$ (1.84 g, 1.6 mmoles, 0.005 eq), sodium carbonate (42.8 g, 404 mmoles, 1.3 eq), 52 (55.5 g, 320.6 mmoles, 1.0 eq), p-fluorophenylboronic acid (53.8 g, 384.7 mmoles, 1.2 eq), followed by 1.3 L denatured EtOH. The reaction was heated to 78° C. with vigorous stirring under $N_2$ overnight. HPLC analysis [$T_{ret}$ 52=10 min, $T_{ret}$ 54=12 min] of the reaction mixture showed that the starting material was completely consumed and a later-eluting peak produced. The reaction was cooled to room temperature and the solvents removed under vacuum. The residue was dissolved in EtOAc, washed, dried ($MgSO_4$), filtered through celite, and concentrated to afford a pale yellow solid 54.

Example 3

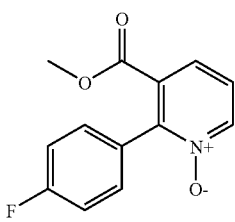

55

2-(4-Fluoro-phenyl)-1-oxy-nicotinic acid methyl ester (55): To a nitrogen purged flask was charged urea hydrogen peroxide (86.9 g, 924 mmoles, 4.0 eq.), the diaryl pyridine 54 (53.4 g, 231 mmoles, 1.0 eq) and 530 mL acetic acid. The bright yellow homogeneous solution was heated to 70–75° C. with vigorous stirring under nitrogen until the HPLC analysis [$T_{ret}$ 54=12 min, $T_{ret}$ 55=10 min] showed >97% completion. The reaction was cooled to room temperature and the contents slowly poured onto 500 g of ice. To the vigorously stirred icy mixture was slowly added 6N NaOH to pH 7 while maintaining a temperature of 30° C. EtOAc and $NaHCO_3$ (solid) were added until an aqueous pH of 8–9 was reached, and the solids dissolved. The layers were separated and the aqueous layer back-extracted with EtOAc. The combined organics were washed with 5% $NaHCO_3$ and then tested by peroxide test strips for the presence of oxidant. If the organic layer was positive for peracid, the bicarbonate washes were repeated until the test was negative. Once negative for peracid, the combined organics were dried ($MgSO_4$), filtered, and concentrated to a pale yellow solid 55.

Example 4

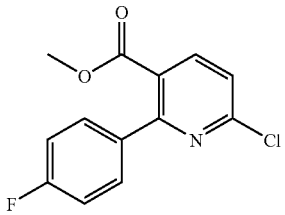

41

6-Chloro-2-(4-fluoro-phenyl)-nicotinic acid methyl ester (41): To a nitrogen purged flask was charged the N-Oxide 55 (45 g, 182 mmoles, 1.0 eq) followed by 300 mL dichloroethane. The phosphorous oxychloride (101 mL, 1080 mmoles, 6 eq) was added all at once, causing an immediate rise in temperature from 17 to 19° C. followed by gradual warming after that. The solution was heated under nitrogen to 70–75° C. until HPLC analysis [$T_{ret}$ 55=10 min, $T_{ret}$ 41=17 min] showed >94% completion. The reaction was cooled to room temperature and the contents concentrated under vacuum to remove most of the POCl$_3$. The remainder was quenched by slowly pouring onto 450 g of ice. After melting the ice, the product was extracted into methylene chloride. The combined organics were dried (MgSO$_4$), filtered through silica, eluted with methylene chloride, and concentrated to a solid 41.

Example 5

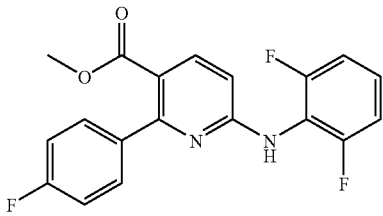

44

6-(2,6-Difluoro-phenylamino)-2-(4-fluoro-phenyl)-nicotinic acid methyl ester (44): To a nitrogen purged flask was charged palladium acetate (13.2 g, 59 mmoles, 0.04 eq), racemic BINAP (36.6 g, 59 mmoles, 0.04 eq), followed by 1.9 L toluene. The heterogeneous slurry was heated to 50° C. under nitrogen for 2 hours, cooled to 30° C., then the pyridyl chloride 41 (386.4 g, 1.45 moles, 1.0 eq) and Boc-2,6-difluoroaniline 42 (386.4 g, 1.69 moles, 1.2 eq), and K$_3$PO$_4$ (872 g, 4.1 moles, 2.8 eq) were added all at once followed by a 1.9 L toluene rinse. The heterogeneous reaction mixture was heated to 100° C. overnight and monitored by HPLC. When the reaction showed complete conversion to 43 by HPLC [$T_{ret}$ 41=17 min, $T_{ret}$ 43=20.5 min, $T_{ret}$ 44=17.6 min, monitored at 229 nm] (usually between 18–20 hours) the reaction was cooled to room temperature and the contents diluted with 1.94 L EtOAc. To this was added 1×1.94 L of 6N HCl, and both layers were filtered through celite. The celite wet cake was rinsed with 2×1.9 L EtOAc. The layers were separated and the organic layer washed with 1×1.9 L of brine, dried (MgSO$_4$), filtered and concentrated to a brown, viscous oil. To remove the Boc-protecting group, the oil was dissolved in 1.94 L of methylene chloride and 388 mL TFA was added. The reaction was stirred overnight to facilitate Boc removal. The volatiles were removed in vacuo, EtOAc (1.9 L) and sufficient quantity of 1 or 6N NaOH was added until the pH was 2–7. Then a sufficient quantity of 5% NaHCO$_3$ was added to bring the pH to 8–9. The organic layer was separated and washed with 1×5% NaHCO$_3$, dried (MgSO$_4$), filtered an concentrated to a brown oil/liquid. The crude oil/liquid was azeodried twice with a sufficient quantity of toluene. At times the free base precipitated out resulting in a slurry. The residue was dissolved in 500 mL toluene and 1.6 L 1N HCl/ether solution was added, which resulted in the solids crashing out. Heat was applied until the homogenized/solids broke up. If necessary, 200 mL of EtOAc can be added to facilitate the break up. After cooling, the solid 44 was isolated by vacuum filtration.

Example 6

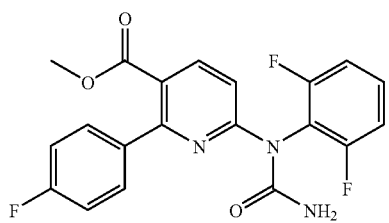

56

6-1-(2,6-Difluoro-phenyl)-ureido]-2-(4-fluoro-phenyl)-nicotinic acid methyl ester (56): To a nitrogen purged flask was charged the amino ester HCl salt of 44 (262 g, 0.67 mole, 1.0 eq), followed by 1.2 L toluene. To the heterogeneous mixture was added phosgene (1.4 L of 1.93 M toluene solution, 2.7 moles, 4.0 eq) and the reaction was heated to 50° C. under nitrogen overnight. The progress of the reaction to form the —NC(O)Cl moiety was monitored by HPLC [$T_{ret}$ 44=17.6 min, $T_{ret}$ carbamoyl intermediate=19.7 min, $T_{ret}$ 56=16.4 min, monitored at 229 nm]. Once the nitrogen was completely reacted, the brown solution was cooled to approximately −52° C., and NH$_4$OH (0.84 L, 12.4 moles, 18.5 eq) was slowly added dropwise. As the addition neared completion a solid formed. The slurry was stirred with 1 L of water and collected by vacuum filtration. The wet cake was washed with 1×390 mL toluene to remove late eluting impurities.

Example 7

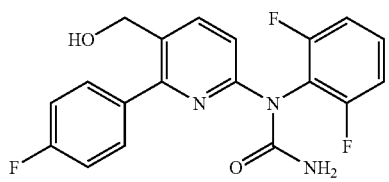

57

1-(2,6-Difluoro-phenyl)-1-[6-(4-fluoro-phenyl)-5-hydroxymethyl-pyridin-2-yl]-urea (57): To a nitrogen purged flask was charged the urea-ester 56 (10.0 g, 24.92 mmol, 1.0 eq) followed by 10 mL THF. The mixture was cooled to 0–5° C. To the cooled solution was added DIBAL-H/THF solution (149.5 mL, 149.5 mmol, 6.0 eq) dropwise over 20–30 minutes. The mixture was stirred at 15–20° C. while the reaction progress was monitored by HPLC [$T_{ret}$ 56=16.4 min, $T_{ret}$ 57=14.0 min, monitored at 229 nm]. The reaction mixture was quenched into cooled (5–10° C.) 15% aqueous $H_2SO_4$ (150 mL). After the quench was completed, the mixture was stirred for 10–15 minutes. To the mixture was added TBME (150 mL). The mixture was heated at 50° C. for 60 minutes. The mixture was cooled to ambient temperature, and the aqueous layer was removed. The organic layer was concentrated to about 35 mL of residual volume. The dilution and concentration process was then repeated. The residual mixture was cooled to 0–2° C., and held at that temperature for 45 minutes. The off-white solid 57 was collected by suction filtration using cold toluene (25 mL) as a rinse solvent. The solid was dried under vacuum at ambient temperature for 3–5 hours to afford 80% corrected yield.

Example 8

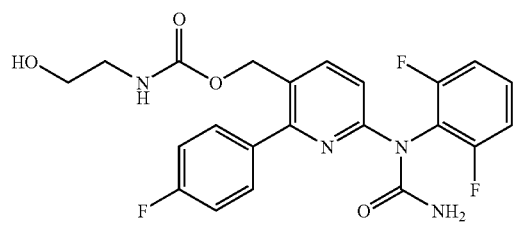

(2-Hydroxy-ethyl)-carbamic acid 6-[1-(2,6-difluoro-phenyl)-ureido]-2-(4-fluoro-phenyl)-pyridin-3-yl methyl ester (58): To a nitrogen purged flask was charged the benzylic alcohol 57 (7.1 g, 19.0 mmoles, 1.0 eq) and CDI (6.2 g, 38.0 mmoles, 2.0 eq) followed by 71 mL THF. The solution was stirred at room temperature for 1–2 hours and then test-quenched into dry acetonitrile/excess ethanolamine. If the activation was not complete, additional CDI can be added until the test quench indicated complete conversion. Once the test-quench showed complete conversion to 58, the reaction was quenched by slowly adding 2.0 eq ethanolamine (0.64 mL, 38 mmoles). The reaction was stirred at room temperature for 2 hours whereupon HPLC analysis [$T_{ret}$ 57=14.2 min, $T_{ret}$ 58=13.6 min, monitored at 229 nm] indicated complete conversion to 58. The THF was removed under vacuum and the residue dissolved in 71 mL ethyl acetate and washed with aqueous NH4Cl solution (2×71 mL) followed by brine (1×71 mL). The organic layer was azeodried with EtOAc (2×71 mL). The residue was reconstituted with 71 mL EtOAc, filtered, and re-concentrated. To the final residue was added 7.1 mL EtOAc and 63 mL of toluene then gently heated to 35–40° C. Upon cooling, a white solid formed which could be isolated by vacuum filtration and washed with cold toluene.

Example 9

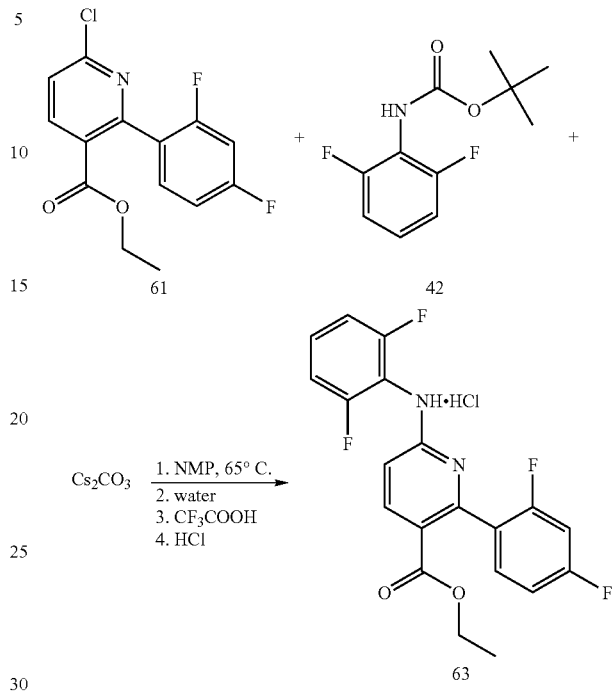

2-(2,4-Difluorophenyl)-6-(2,6-difluorophenylamino)-nicotinic acid ethyl ester (63): In a 1 L, 4-necked, round-bottomed flask equipped with an overhead mechanical stirrer, heating mantle, reflux condenser, and thermocouple was charged 61 (50 g), $Cs_2CO_3$ (150 g) and 0.15 L of NMP. The solution was stirred vigorously and heated to 65° C. at which time to the suspension was added a solution of 42 (60 g) in 0.10 L of NMP over 10 minutes. Heating at 65° C. for 18 hours, HPLC showed ~85% conversion of 61 to the desired Boc adduct. At this time, the temperature was increased to 75° C., and HPLC analysis after heating for an additional 18 hours showed ~97% conversion of 61 to the desired Boc adduct 62 (not shown). The mixture was then cooled to 20 and poured in one portion into 2.0 L of water stirring in a 4-necked, 3 L, round-bottomed flask equipped with an overhead mechanical stirrer and thermocouple. The temperature of the water rose from 22° C. to 27° C. as a result of the addition of the NMP solution. The suspension was then cooled to 15° C. and the tan solid was collected by filtration, rinsed with water and pulled dry on the filter for 2 hours.

In a 2 L, 4-necked, round-bottomed flask equipped with an overhead mechanical stirrer and thermocouple was charged the tan solid and 0.8 L of $CH_2Cl_2$. To the stirred solution was added 70 mL of TFA in one portion. After two hours stirring at ambient temperature, none of the Boc protected material was detected by HPLC, and the mixture was concentrated by rotary evaporation. The oily residue was taken up in 0.7 L EtOAc, and treated with 0.7 L saturated $NaHCO_3$, during which gas was produced. The EtOAc layer was washed with 0.25 L saturated NaCl and concentrated by rotary evaporation. To the resultant brown oil was added 0.2 L EtOAc and the solution treated with HCl in $Et_2O$ (0.4 L of 2.0 M solution) and stirred for 60 minutes. The product 63, a yellow powder, was collected by filtration (70.5% yield).

The product may be recrystallized by heating the crude salt in 4 mL EtOH/g of crude product to reflux, then cooling to ambient temperature.

While we have hereinbefore presented a number of embodiments of this invention, it is apparent that the basic construction can be altered to provide other embodiments which utilize the methods of this invention. Therefore, it will be appreciated that the scope of this invention is to be defined by the claims appended hereto rather than the specific embodiments which have been presented hereinbefore by way of example.

What is claimed is:

1. A process for producing a diaryl amine compound of the formula (I):

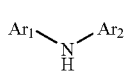
(I)

or a salt thereof,
said process comprising the steps of
(1) coupling a compound of formula (II) with an amine of formula (III) in the presence of an alkali metal salt or a transition metal catalyst:

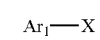
(II)

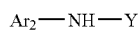
(III)

to form a compound of formula (IV):

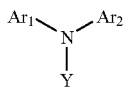
(IV)

and
(2) removing radical Y from the compound of formula (IV) in the presence of an acid;
wherein:
$Ar_1$ and $Ar_2$ are independently Q;
wherein each Q is an aryl or heteroaryl ring system optionally fused to a saturated or unsaturated 5–8 membered sing having 0–4 heteroatoms, wherein either $Ar_1$ or $Ar_2$, is a heteroaryl ring;
wherein Q is optionally substituted at one or more ring atoms with one or more substituents independently selected from halo; $C_1$–$C_6$ aliphatic optionally substituted with $N(R')_2$, OR', $CO_2R'$, $C(O)N(R')_2$, OC(O)N(R')_2$, $NR'CO_2R'$, $NR'C(O)R'$, $SO_2N(R')_2$, N=CH—N(R')_2$, or $OPO_3H_2$; $C_1$–$C_6$ alkoxy optionally substituted with $N(R')_2$, OR', $CO_2R'$, $C(O)N(R')_2$, OC(O)N(R')_2$, $NR'CO_2R'$, $NR'C(O)R'$, $SO_2N(R')_2$, N=CH—N(R')_2$, or $OPO_3H_2$; $Ar_3$; $CF_3$; $OCF_3$; OR'; SR'; $SO_2N(R')_2$; $OSO_2R'$; $SCF_3$; $NO_2$; CN; $N(R')_2$; $CO_2R'$; $CO_2N(R')_2$; $C(O)N(R')_2$; $NR'C(O)R'$; $NR'CO_2R'$; $NR'C(O)C(O)R'$; $NR'SO_2R'$; $OC(O)R'$; $NR'C(O)R^2$; $NR'CO_2R^2$; $NR'C(O)C(O)R^2$; $NR'C(O)N(R')_2$; $OC(O)N(R')_2$; $NR'SO_2R^2$; $NR'R^2$; $N(R^2)_2$; $OC(O)R^2$; $OPO_3H_2$; and N=CH—N(R')_2$;
R' is selected from hydrogen; $C_1$–$C_6$ aliphatic; or a 5–6 membered carbocyclic or heterocyclic ring system optionally substituted with 1 to 3 substituents independently selected from halo, $C_1$–$C_6$ alkoxy, cyano, nitro, amino, hydroxy, and $C_{1-C6}$ aliphatic;
$R^2$ is a $C_1$–$C_6$ aliphatic optionally substituted with $N(R')_2$, OR', $CO_2R'$, $C(O)N(R')_2$ or $SO_2N(R')_2$; or a carbocyclic or heterocyclic ring system optionally substituted with $N(R')_2$, OR', $CO_2R'$, $C(O)N(R')_2$ or $SO_2N(R')_2$;
wherein $Ar_3$ is an aryl or heteroaryl ring system optionally fused to a saturated or unsaturated 5–8 membered ring having 0–4 heteroatoms;
wherein $Ar_3$ is optionally substituted at one or more ring atoms with one or more substituents independently selected from halo; $C_1$–$C_6$ aliphatic optionally substituted with $N(R')_2$, OR', $CO_2R'$, $C(O)N(R')_2$, OC(O)N(R')_2$, $NR'CO_2R'$, $NR'C(O)R'$, $SO_2N(R')_2$, N=C—N(R')_2$, or $OPO_3H_2$; $C_1$–$C_6$ alkoxy optionally substituted with $N(R')_2$, OR', $CO_2R'$, $C(O)N(R')_2$, OC(O)N(R')_2$, $SO_2N(R')_2$, $NR'CO_2R$, $NR'C(O)R'$, N=C—N(R')_2$, or $OPO_3H_2$; $CF_3$; $OCF_3$; OR'; SR'; $SO_2N(R')_2$; $OSO_2R'$; $SCF_3$; $NO_2$; CN; $N(R')_2$; $CO_2R'$; $CO_2N(R')_2$; $C(O)N(R')_2$; $NR'C(O)R'$; $NR'CO_2R'$; $NR'C(O)C(O)R'$; $NR'SO_2R'$; $OC(O)R'$; $NR'C(O)R^2$; $NR'CO_2R^2$; $NR'C(O)C(O)R^2$; $NR'C(O)N(R')_2$; $OC(O)N(R')_2$; $NR'SO_2R^2$; $NR'R^2$; $N(R^2)_2$; $OC(O)R^2$; $OPO_3H_2$; and —N=C—N(R')_2$;
X is a leaving group;
Y is —C(O)—O-Z; and
Z is $C_1$–$C_6$ aliphatic, benzyl, Fmoc, —$SO_2R'$ or Q, provided that Q is not substituted with X or alkyne.

2. The process according to claim 1, wherein the process is performed using a transition metal catalyst.

3. The process according to claim 2, wherein the transition metal catalyst comprises palladium.

4. The process according to claim 3 wherein the catalyst is $PdL_n$, wherein
each L is independently selected from —OAc, —O-tolyl, halogen, $PPh_3$, dppe, dppf, dba, and BINAP; and
n is an integer from 0–4.

5. The process according to claim 2, wherein the step of coupling a compound of formula (II) with an amine of formula (III) is performed in the presence of a base.

6. The process according to claim 5, wherein the base is selected from KOtBu, NaOtBu, $K_3PO_4$, $Na_2CO_3$, and $Cs_2CO_3$.

7. The process according to claim 1, wherein the process is performed using an alkali metal salt.

8. The process according to claim 7, wherein the alkali metal salt is selected from salts of potassium, rubidium, or cesium ions.

9. The process according to claim 8, wherein the alkali metal salt is selected from potassium carbonate or cesium carbonate.

10. The process according to claim 9, wherein the alkali metal salt is cesium carbonate.

11. The process according to claim 1, wherein X is selected from the group consisting of —Cl, —Br, —I. —F, —OTf, —OTs, iodonium, and diazo.

12. The process according to claim 1, wherein Y is Boc.

13. The process according to claim 1 for producing a diaryl amine compound of the formula:

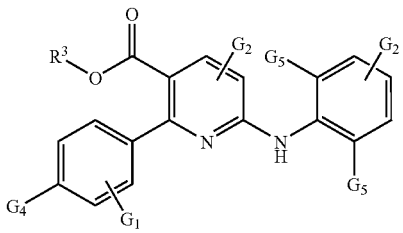

comprising the steps of (1) coupling a compound of formula 21 with an amine of formula 22 in the presence of an alkali metal salt or a transition metal catalyst, and (2) removing radical Y from the resultant compound in the presence of an acid:

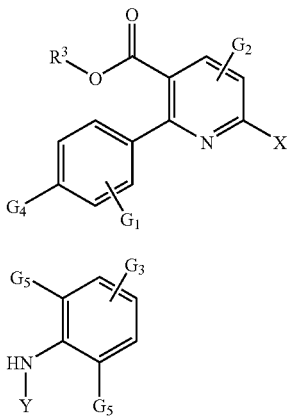

wherein:
R$_3$ is selected from aliphatic, aryl, or aryl substituted with aliphatic, aryl, nitro, CN, CO$_2$R', CO$_2$N(R')$_2$, OR', NCO$_2$R', NR'C(O)N(R')$_2$, and OC(O)N(R')$_2$;
provided that R$_3$ is not t-butyl; and
G$_1$, G$_2$, G$_3$, G$_4$, and G$_5$ are independently selected from hydrogen, aliphatic, aryl, substituted aryl, nitro, CN, OR', CO$_2$R', CO$_2$N(R')$_2$, NR'CO$_2$R', NR'C(O)N(R')$_2$, OC(O)N(R')$_2$, F, Cl, Br, I, O-TOs, O-Ms, OSO$_2$R', and OC(O)R'.

14. The process according to claim 13, wherein the process is performed using a transition metal catalyst.

15. The process according to claim 14, wherein the transition metal catalyst comprises palladium.

16. The process according to claim 15 wherein the catalyst is PdL$_n$, wherein
each L independently is selected from —OAc, —O-tolyl, halogen, PPh$_3$, dppe, dppf, dba, and BINAP; and n is an integer from 0–4.

17. The process according to claim 14, wherein the step of coupling a compound of formula 21 with an amine of formula 22 is performed in the presence of a base.

18. The process according to claim 17, wherein the base is selected from KOtBu. NaOtBu, K$_3$PO$_4$, Na$_2$CO$_3$, and Cs$_2$CO$_3$.

19. The process according to claim 13, wherein the process is performed using an alkali metal salt.

20. The process according to claim 19, wherein the alkali metal salt is selected from salts of potassium, rubidium, or cesium ions.

21. The process according to claim 20, wherein the alkali metal salt is selected from potassium carbonate or cesium carbonate.

22. The process according to claim 21, wherein the alkali metal salt is cesium carbonate.

23. The process according to claim 13, wherein X is selected from the group consisting of —Cl, —Br, —I, —F, —OTf, —OTs, iodonium, and diazo.

24. The process according to claim 13, wherein Y is Boc.

25. The process according to claim 1 for producing a diaryl amine compound of the formula:

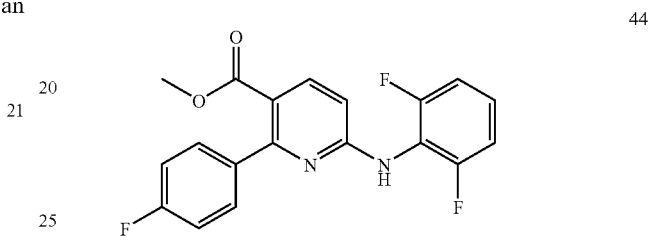

or a salt thereof,
said process comprising the steps of (1) coupling a compound of formula 41a with an amine of formula 42a in the presence of an alkali metal salt or a transition metal catalyst, and (2) removing radical Y from the resultant compound in the presence of an acid:

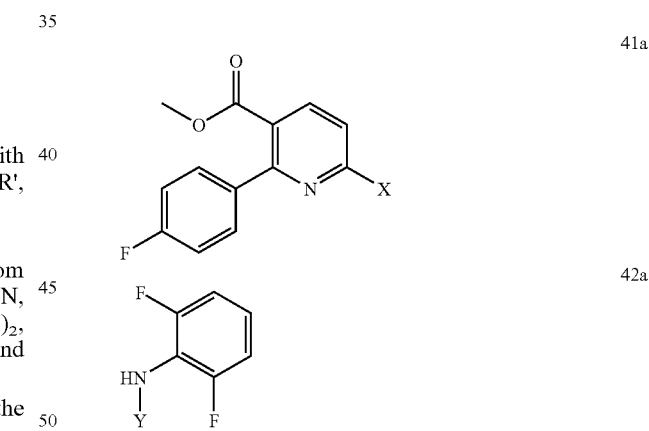

26. The process according to claim 25, wherein the process is performed using a transition metal catalyst.

27. The process according to claim 26, wherein the transition metal catalyst comprises palladium.

28. The process according to claim 27 wherein the catalyst is PdL$_n$, wherein
each L is independently selected from —OAc, —O-tolyl, halogen, PPh$_3$, dppe, dppf, dba, and BINAP; and n is an integer from 0–4.

29. The process according to claim 26, wherein the step of coupling a compound of formula 41a with an amine of formula 42a is performed in the presence of a base.

30. The process according to claim 29, wherein the base is selected from KOtBu, NaOtBu, K$_3$PO$_4$, Na$_2$CO$_3$, and Cs$_2$CO$_3$.

31. The process according to claim 25, wherein the process is performed using an alkali metal salt.

32. The process according to claim 31, wherein the alkali metal salt is selected from salts of potassium, rubidium, or cesium ions.

33. The process according to claim 32, wherein the alkali metal salt is selected from potassium carbonate or cesium carbonate.

34. The process according to claim 33, wherein the alkali metal salt is cesium carbonate.

35. The process according to claim 25, wherein X is selected from the group consisting of —Cl, —Br, —I, —F, —OTf, —OTs, iodonium, and diazo.

36. The process according to claim 25, wherein Y is Boc.

37. The process according to claim 1 for producing a diaryl amine compound of the formula:

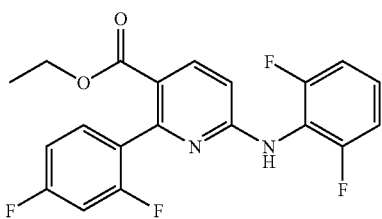

63 or a salt thereof,
said process comprising the steps of (1) coupling a compound of formula 61a with an amine of formula 42a in the presence of an alkali metal salt or a transition metal catalyst, and (2) removing radical Y from the resultant compound in the presence of an acid:

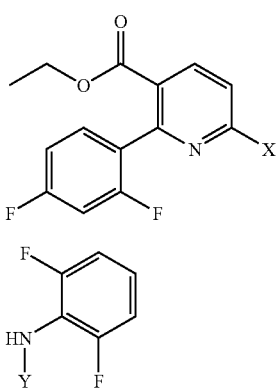

61a

42a

38. The process according to claim 37, wherein the process is performed using a transition metal catalyst.

39. The process according to claim 38, wherein the transition metal catalyst comprises palladium.

40. The process according to claim 39, wherein the catalyst is PdL$_n$, wherein
each L is independently selected from —OAc, —O-tolyl, halogen, PPh$_3$, dppe, dppf, dba, and BINAP; and a is as integer from 0–4.

41. The process according to claim 38, wherein the step of coupling a compound of formula 61a with an amine of formula 42a is performed in the presence of a base.

42. The process according to claim 41, wherein the base is selected from KOtBu, NaOtBu, K$_3$PO$_4$, Na$_2$CO$_3$, and Cs$_2$CO$_3$.

43. The process according to claim 37, wherein the process is performed using an alkali metal salt.

44. The process according to claim 43, wherein the alkali metal salt is selected from salts of potassium, rubidium, or cesium ions.

45. The process according to claim 44, wherein the alkali metal salt is selected from potassium carbonate or cesium carbonate.

46. The process according to claim 45, wherein the alkali metal salt is cesium carbonate.

47. The process according to claim 37, wherein X is selected from the group consisting of —Cl, —Br, —I, —F, —OTf, —OTs, iodonium, and diazo.

48. The process according to claim 37, wherein Y is Boc.

49. The process according to claim 37 for producing a diaryl amine compound of the formula:

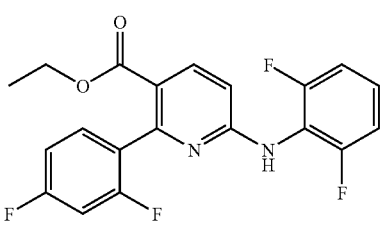

63 or a salt thereof,
said process comprising the steps of (1) coupling a compound of formula 61 with an amine of formula 42 in the presence of an alkali metal salt or a transition metal catalyst, and (2) removing the Boc group from the coupled amine in the presence of an acid:

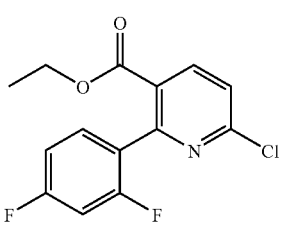

61

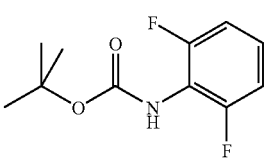

42

50. The process according to claim 49 wherein the process is performed using cesium carbonate.

51. The process according to claim 49 further comprising the steps of:
(a) reacting the compound of formula 63 with a base; and (b) acidifying the reaction mixture formed in step (a) to produce a compound of the formula 75:

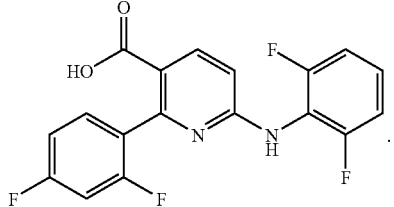

75

52. The process according to claim 51 wherein the base in step (a) is NaOH.

53. The process according to claim 51 wherein the acid in step (b) is HCl.

54. The process according to claim 51 further comprising the steps of:

(c) reacting the compound of formula 75 with diphosgene; and (d) treating the reaction mixture formed in step (c) with NH₄OH to produce a compound of the formula 76:

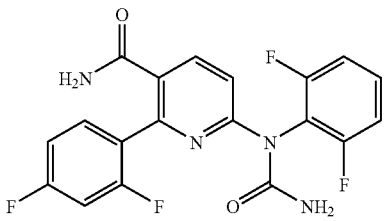

76

55. The process according to claim 1, wherein the acid is selected from the group consisting of HCl, HBr, HI and an organic acid.

56. The process according to claim 13, wherein the acid is selected from the group consisting of HCl, HBr, HI and an organic acid.

57. The process according to claim 25, wherein the acid is selected from the group consisting of HCl, HBr, HI and an organic acid.

58. The process according to claim 37, wherein the acid is selected from the group consisting of HCl, HBr, HI and an organic acid.

59. The process according to claim 49, wherein the acid is selected from the group consisting of HCl, HBr, HI and an organic acid.

* * * * *